US005575763A

United States Patent [19]

Nagata et al.

[11] Patent Number: 5,575,763
[45] Date of Patent: Nov. 19, 1996

[54] CERVICAL ORTHOSIS

[75] Inventors: Hiroto Nagata, 8-1, Takadai 4-chome, Nagaokakyo-shi, Kyoto 617, Japan; Shoichi Komaba, Oita; Toru Nagano, Katawo Toyonaka; Hidenori Kanezaki, Osaka, all of Japan

[73] Assignees: Toshinobu Onomura, Nishinomiya; Hiroto Nagata, Nagaokakyo; Kawamura Gishi Co., Ltd., Osaka, all of Japan

[21] Appl. No.: 312,542

[22] Filed: Sep. 26, 1994

[30] Foreign Application Priority Data

Mar. 24, 1994 [JP] Japan ................................. 6-054113
Aug. 31, 1994 [JP] Japan ................................. 6-207452

[51] Int. Cl.[6] ................................................ A61F 5/00
[52] U.S. Cl. .............................. 602/18; 602/17; 602/19; 606/241; 128/875
[58] Field of Search ............................. 602/17, 18, 19; 606/241; 128/DIG. 23, 97.1, 875; 2/44, 45

[56] References Cited

U.S. PATENT DOCUMENTS

| | | | |
|---|---|---|---|
| 3,170,659 | 2/1965 | Wood . | |
| 3,359,976 | 12/1967 | Laval, Jr. | 602/19 X |
| 4,477,041 | 10/1984 | Dunne | 244/122 |
| 4,628,913 | 12/1995 | Lerman | 602/18 |
| 4,899,736 | 2/1990 | Nesbitt . | |
| 5,109,835 | 5/1992 | McDonald et al. | 602/241 |
| 5,205,813 | 4/1993 | Schmidt | 602/17 |
| 5,248,293 | 9/1993 | Hubbard et al. | 602/19 X |
| 5,409,450 | 4/1995 | Donelson | 602/17 X |

FOREIGN PATENT DOCUMENTS

| | | | |
|---|---|---|---|
| 660679 | 5/1979 | U.S.S.R. | 602/18 |
| 1602512 | 10/1990 | U.S.S.R. | 602/19 |

*Primary Examiner*—Richard J. Apley
*Assistant Examiner*—Kim M. Lee
*Attorney, Agent, or Firm*—Oblon, Spivak, McClelland, Maier & Neustadt, P.C.

[57] ABSTRACT

A cervical orthosis has front and rear cervical orthosis members. The front cervical orthosis member includes a chest support abutting against the region from the shoulders to the chest. Two front supporting portions are arranged from the chest support along both side portions of the anterior of neck and both side portions of the head. The rear cervical orthosis member includes a back support abutting against the region from the shoulders to the back. Two rear supporting portions are arranged from the back support along both side portions of the posterior of neck. An occipital region brace portion extends further upward from the upper end of each of the rear supporting portions so as to brace the occipital region. The cervical orthosis also has a forehead brace member abutting against the forehead and bracing the frontal region, and a cheek brace member arranged on the internal surfaces of the front supporting portions so as to brace the cheeks without disturbing the movement of the mandible.

14 Claims, 10 Drawing Sheets

CERVICAL ORTHOSIS

BACKGROUND OF THE INVENTION

1. Field of the Invention

The present invention relates to a cervical orthosis used for bracing cervical spine and the head, and for permitting them to rest because of cervical spinal injury and operations involved therein.

2. Description of the Related Art

Figure 13:
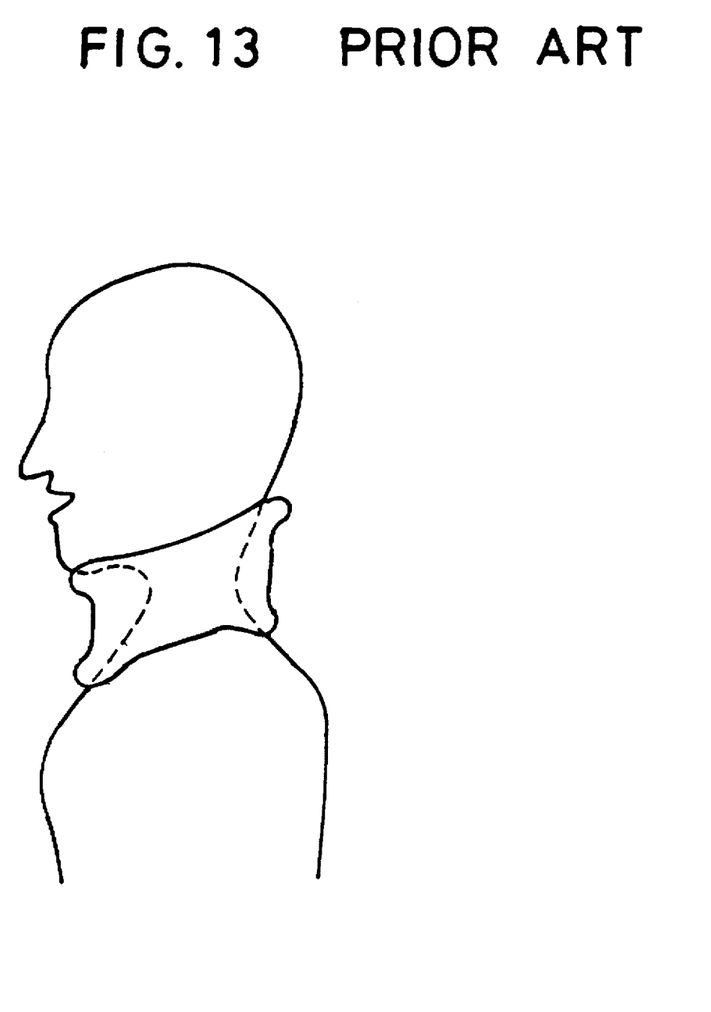
FIG. 13 is a side view of an example of the construction of a conventional cervical orthosis.

Among segments of the spine, the cervical spine has a wide movement range, and from an anatomical point of view, it has complicated construction and functions. According to this fact, it is necessary to brace the wide region from the head and the neck to the trunk in order to securely brace the cervical spine. In view of such an object, a conventional cervical orthosis is generally constructed to wind around the neck and to support the mandible from a downward angle so as to brace cervical spine, as illustrated in, for example, FIG. 13. Although various improvements have been made, for example, by adding adjustment functions to the above-mentioned basic construction, all the resultant braces end up restraining the mandible in order to consolidate further bracing performance.

Such conventional cervical orthoses present the following problems. The use of such orthosis considerably restricts the opening of the mouth by the patient, thus extremely inconveniencing movements necessary in daily life, such as talking or eating a meal, thereby making the patient uncomfortable.

SUMMARY OF THE INVENTION

Accordingly, in view of the above-noted problems inherent in the conventional braces, the major object of the present invention is to provide a cervical orthosis which does not restrict the opening of the mouth by the patient while talking or eating a meal, and which is capable of bracing cervical spine safely and reliably.

In order to solve the foregoing problems and achieve the above objects, the present invention provides a cervical orthosis comprising: (a) a front cervical orthosis member including a chest support abutting against the region from the shoulders to the chest, and two front supporting portions arranged from the chest support along both side portions of the anterior of neck and both side portions of the head; (b) a rear cervical orthosis member including a back support abutting against the region from the shoulders to the back, two rear supporting portions arranged from the back support along both side portions of the posterior of neck, and an occipital region brace portion extending further upward from the upper end of each of the rear supporting portions so as to brace the occipital region; (c) a forehead brace member abutting against the forehead and bracing the frontal region of head; and (d) a cheek brace member arranged on the internal surfaces of the front supporting portions so as to brace the cheeks without disturbing the movement of the mandible.

Cushioning materials (mainly formed of a flexible urethane form, a cloth mat, or the like) may preferably be attached to the internal surfaces of the front and rear cervical orthosis members. Such cushioning materials may preferably be detachable using VELCRO fastener used as detachable tape, a hook, or the like.

The cheek brace member may preferably be anchored to the internal surfaces of the front supporting portions via VELCRO fastener so that it is adjustable to be positioned.

A pair of projections may preferably be arranged at front sides of the occipital region brace portion so that they are vertically adjustable at a desired angle.

The forehead brace member may include a band-like belt and a pad detachably attached to the band-like belt by way of example.

The present invention may include an extension element at the bottom of the chest support and/or the back support so as to extend the chest support and/or the back support.

The present invention may include an expansion and contraction element at the front supporting portions and/or the rear supporting portions so as to adjust the length of the supporting portions.

An interconnecting element, which length is adjustable, may preferably interconnect the parts of the front supporting portions corresponding to the mandible.

The present invention may preferably be constructed as follows. A pin may be arranged on the external surface of the front end of the occipital region brace portion, while a mating hole is arranged on the upper end of each of the front supporting portions. The pin may be inserted into the mating hole, thereby combining the occipital region brace portion and each of the front supporting portions and pivotally opening and closing them about the pin in the forward-backward direction. The pin and the mating hole may reversely be attached to the occipital region brace portion and the front supporting portions.

A band-like belt may preferably be arranged to interconnect the front and rear cervical orthosis members.

Since the cervical orthosis of the present invention does not restrain the mandible, the patient is able to comfortably open the mouth necessary in daily life, such as talking or eating a meal while wearing such a cervical orthosis. The respective members and portions of the cervical orthosis are adjustable to be compatible with the patient, thus enhancing comfortable fitting and achieving correct bracing performance, substantially without pressurizing and discomforting the patient. Further, since the anterior and posterior of neck, which are most likely to be sectioned during an operation, are not covered with such a brace, the patient can go under an operation while wearing the brace. It is also possible to easily perform the dressing change after an operation, free from pressurizing the wounds after the operation.

The above and other objects, features and advantages of the present invention will become apparent from the following description read in conjunction with the accompanying drawings in which like reference numerals designate the same elements.

DESCRIPTION OF THE PREFERRED EMBODIMENTS

Figure 1:
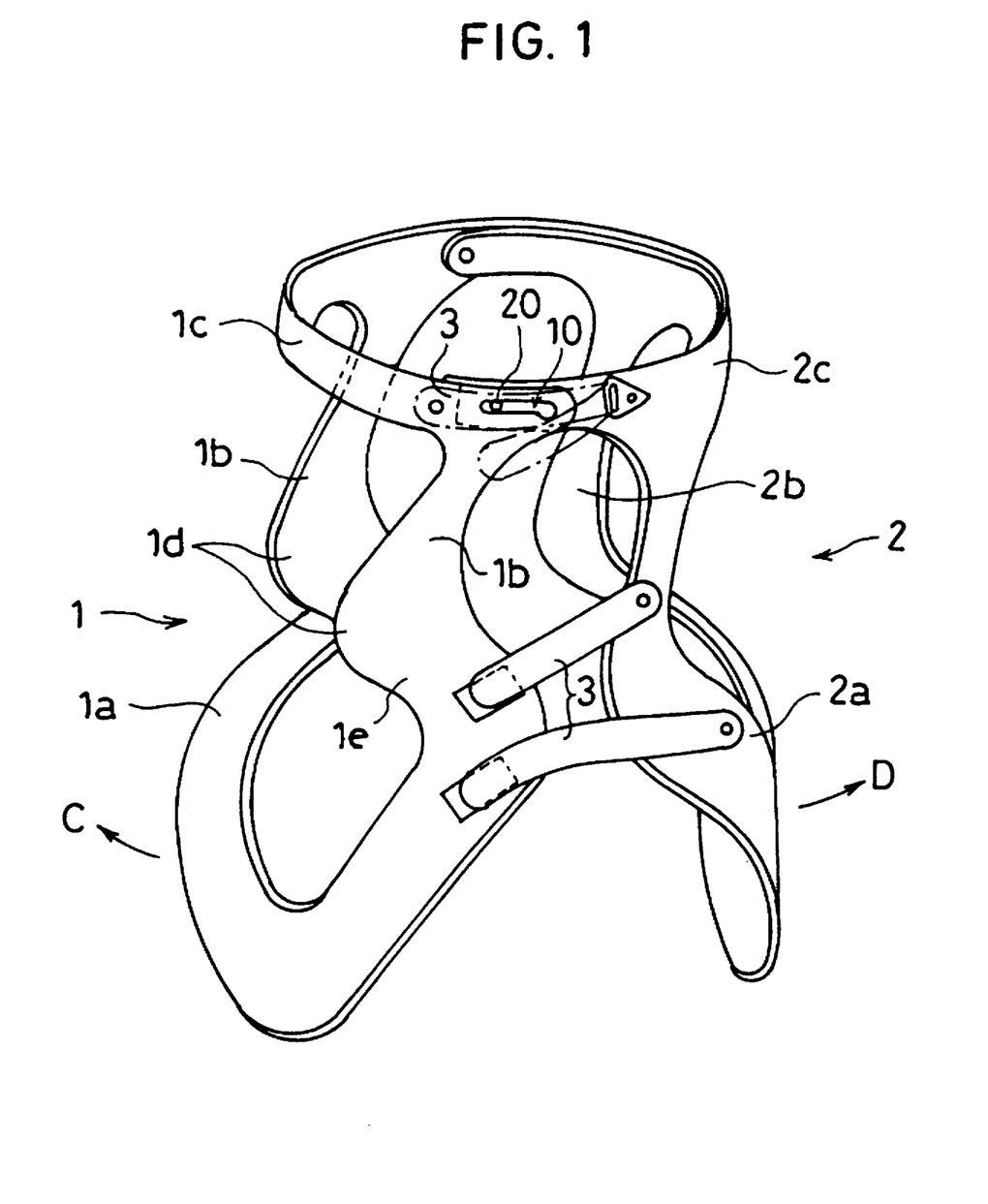
FIG. 1 is a perspective view of a first embodiment of a cervical orthosis according to the present invention.

Referring to FIG. 1, the cervical orthosis mainly comprises a front cervical orthosis member 1, a rear cervical orthosis member 2 and band-like belts 3 for interconnecting these brace members 1 and 2. The front and rear cervical orthosis members 1 and 2 are integrally formed by thermoplastic resin, such as polyester resin, polyvinyl chloride resin, polyolefin resin, for example, polyethylene and polypropylene, acrylic resin, polyurethane resin, polyamide resin, or alternatively, formed by thermoset resin, such as urea resin, melamine resin or epoxy resin.

The front cervical orthosis member 1 is obtained by integrally forming a forehead brace portion 1c to abut against a forehead, cheek supporting portions 1d, which lower end is opened for the mandible, for supporting the cheeks from an oblique downward angle, an anterior-of-neck brace portion 1e to abut against both side portions of the anterior of neck, and a chest support 1a to abut against the region from the shoulders to the chest.

On the other hand, the rear cervical orthosis member 2 is obtained by integrally forming an occipital region brace portion 2c to abut against the occipital region, the posterior-of-neck brace portion 2b to abut against the posterior of neck, and a back support 2a to abut against the region from the shoulders to the back.

Projections 20 are provided for both ends of the upper portion of the rear cervical orthosis member 2, while slits 10 are arranged on both ends of the upper portion of the front cervical orthosis member 1 so as to be engaged with such projections 20. The front and rear cervical orthosis members 1 and 2 can be combined by fitting the projections 20 into the slits 10. The slits 10 function to adjust the circumferential length according to the size of the head. The projections 20 function to pivot about both sides of the head so as to open and close the cervical orthosis, thereby enhancing easy wearing of the brace.

That is, this orthosis can be opened in the directions indicated by the arrows C and D shown in FIG. 1, while it maintains the state in which the front and rear cervical orthosis members 1 and 2 are combined. Making use of this advantage, the orthosis in the opened state is put on from the head of a patient, and the positions of the projections 20 in the slits 10 are adjusted according to the size of the head, thereby comfortably fitting the cervical orthosis to the patient while covering the region from the head to the cervical spine.

The band-like belts 3 can be used for securely interconnecting the front and rear cervical orthosis members 1 and 2 which have been put on the patient. VELCRO fastener is affixed to the band-like belts 3 so that the brace members 1 and 2 can be interconnected according to the thickness of the chest of the patient.

Figure 2:
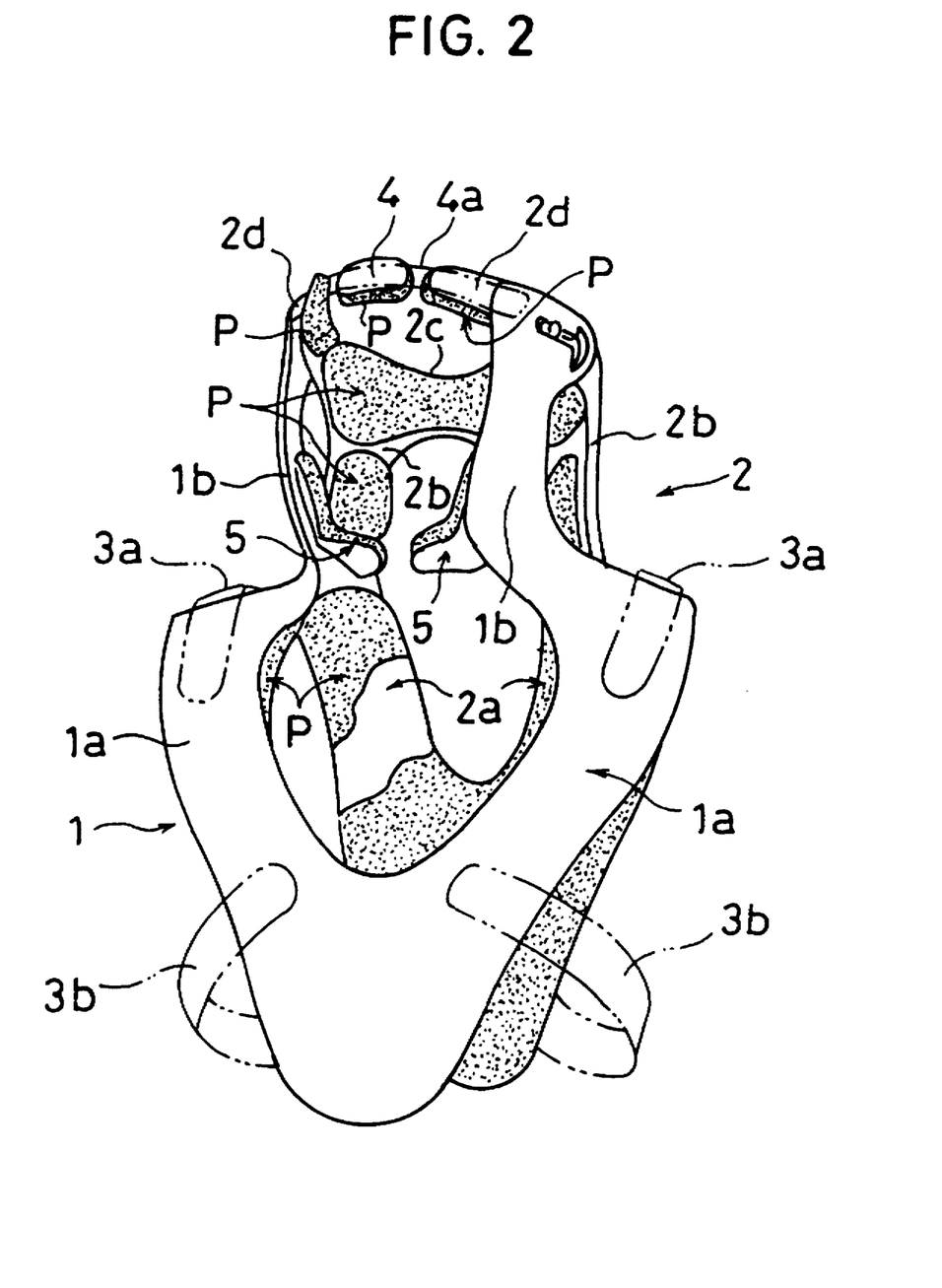
FIG. 2 is a perspective view of a second embodiment of a cervical orthosis according to the present invention.

FIG. 2 is a perspective view of a second embodiment of a cervical orthosis according to the present invention. Components corresponding to those in FIG. 1 have been given the same reference numerals as in FIG. 1. Referring to FIG. 2, the front cervical orthosis member 1 comprises a generally V-shaped chest support 1a to abut against the region from the shoulders to the chest, and two front supporting portions 1b, 1b raised from the top end of the chest support 1a to be arranged along both side portions of the anterior of neck and the side portions of the head.

On the other hand, the rear cervical orthosis member 2 comprises a generally V-shaped back support 2a to abut against the region from the shoulders to the back, and two rear supporting portions 2b, 2b raised from the top end of the back support 2a to be arranged along the side portions of the neck and the side portions of the occipital region. Further above the rear supporting portions 2b, 2b, the occipital region brace portion 2c generally formed in a semi-circular shape is arranged to cover the occipital region so as to brace the occipital bone. A pair of projections 2d, 2d are also extended from the rear cervical orthosis member 2 to the forehead. A forehead brace member 4 is arranged so as to be interconnected to the pair of projections 2d, 2d and the front supporting portions 1b, 1b.

The forehead brace member 4 is allowed to abut against the forehead and to communicate with the pair of projections 2d, 2d and the upper ends of the front supporting portions 1b, 1b, thereby bracing the head in a ring-like form. The forehead brace member 4 is formed of a band-like belt 4a having VELCRO fastener embedded therein and a pad P detachably attached to the band-like belt 4a.

Cushioning pads P (mainly formed of a flexible urethane form, a cloth mat, and the like) are also attached to the internal surfaces of the front and rear cervical orthosis members 1 and 2. Such pads can be attached and detached to/from the internal surfaces of the brace members 1 and 2 using VELCRO fastener, hooks, or the like.

Cheek brace pads 5, 5 are arranged as cheek brace members in the region from the cheeks to the mandible inside the front supporting portions 1b so as to brace the cheeks and to allow free movement of the mandible. As illustrated in FIG. 3, such cheek brace pads 5, 5 can be shaped and located according to the degree of injury of the patient.

Figure 3A:
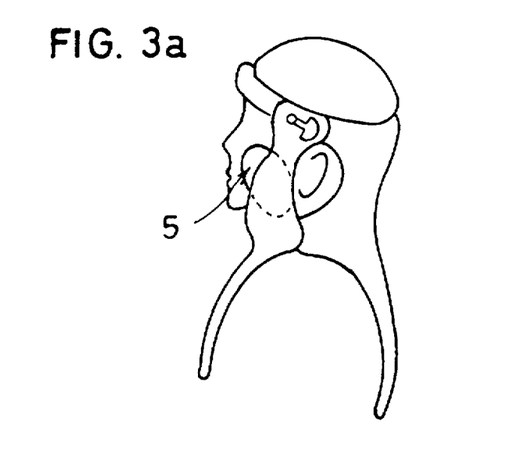
FIG. 3 is a perspective view of cheek brace pads being attached to the cheeks according to the second embodiment.

FIG. 3(a) illustrates the cheek brace pads 5, 5 when the cervical spinal injury is serious. In such a case, large cheek brace pads are used and located to forwardly project from the front supporting portions 1b, 1b so that they can support the zygoma.

Figure 3B:
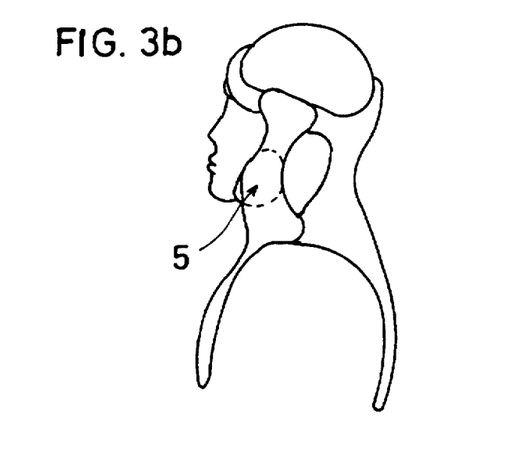

FIG. 3(b) illustrates the cheek brace pads 5, 5 when the cervical spinal injury is intermediate. In such a case, it is sufficient that the cheek brace pads are sized small enough to be accommodated within the width of the front supporting portions 1b, 1b, and such pads are located to support the cheeks from an oblique downward angle.

Figure 3C:
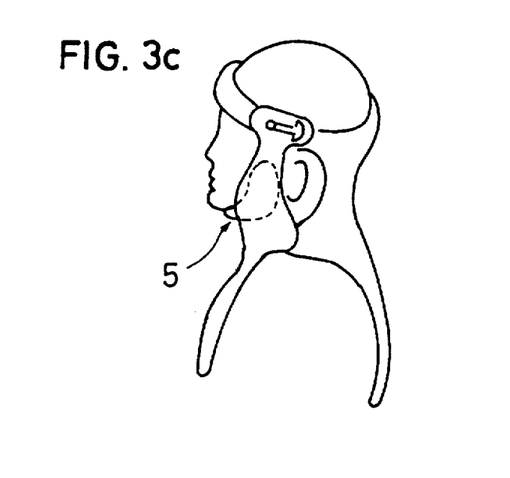

FIG. 3(c) illustrates the cheek brace pads 5, 5 when the cervical spine is not so injured. In such a case, the cheek brace pads each comprise a pad portion P, a resin-formed support plate for maintaining the lower end of the pad P in an L-shape so that the pad P can be along by the shape of the mandible, and VELCRO fastener affixed to the reverse surface of the support plate. The cheek brace pads are located to be in contact with the mandible. It should be noted that although the lower ends of the cheek brace pads are brought into contact with the mandible, such contact is not for restricting the movement of the mandible, but for urging it to separate from throat molds (throat pads), that is, for urging what is called, "the active correcting force". VELCRO fastener is preferably affixed to the internal surfaces of the front supporting portions 1b, 1b so that the location of the cheek brace pads 5, 5 can be adjusted.

Figure 4:
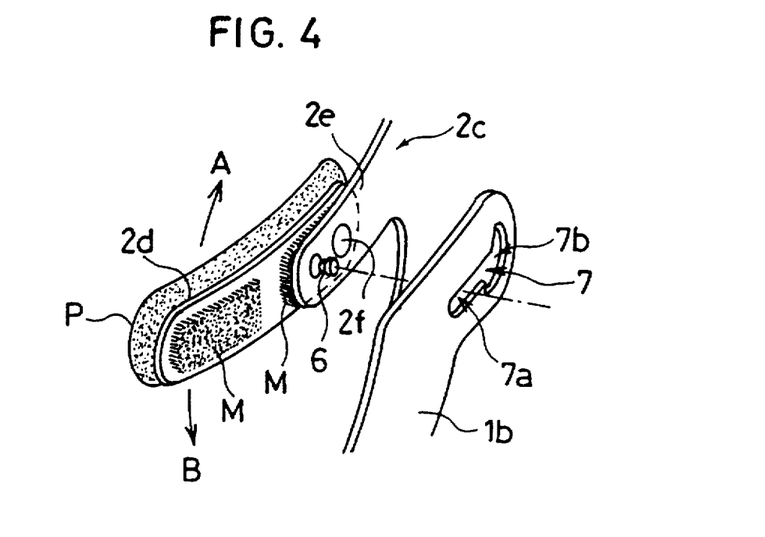
FIG. 4 is an enlarged perspective view of the construction of the upper ends of front and rear supporting portions illustrated in FIG. 2.

As shown in FIG. 4, a projection portion 2e is formed on the front end of the occipital region brace portion 2c of the rear cervical orthosis member 2, and a pin 6 having a cross section generally in the shape of T is laterally arranged on the external surface of the projection portion 2e. On the other hand, a mating hole 7 comprising a slit 7a and a semi-circular notch 7b extending from the rear end of the slit 7a are formed on the upper end of the front cervical orthosis member 1. The above-noted pin 6 is inserted into the semi-circular notch 7b and then is introduced into the front end of the slit 7a, thereby combining the front and rear cervical orthosis members 1 and 2. The combined brace can be pivotally opened and closed about the pin 6 in the forward-backward direction. The slit 7a functions to adjust the circumferential length of the brace according to the size of the head of the patient.

The rear end of the foregoing projection 2d is pivoted to the projection portion 2e via an interconnecting pin 2f so as to be tiltable in the directions indicated by the arrows A and B. Besides, VELCRO fastener M is affixed to the external surface of the projection 2d and the internal surface of the projection portion 2e, thereby fixing the projection 2d to the projection portion 2e at a desired angle. VELCRO fastener M is affixed to the front end of the projection 2d so as to attach the band-like belt 4a of the forehead brace member 4. The foregoing interconnecting pin 2f and the pin 6 may be comprised of a single part.

Figure 5:
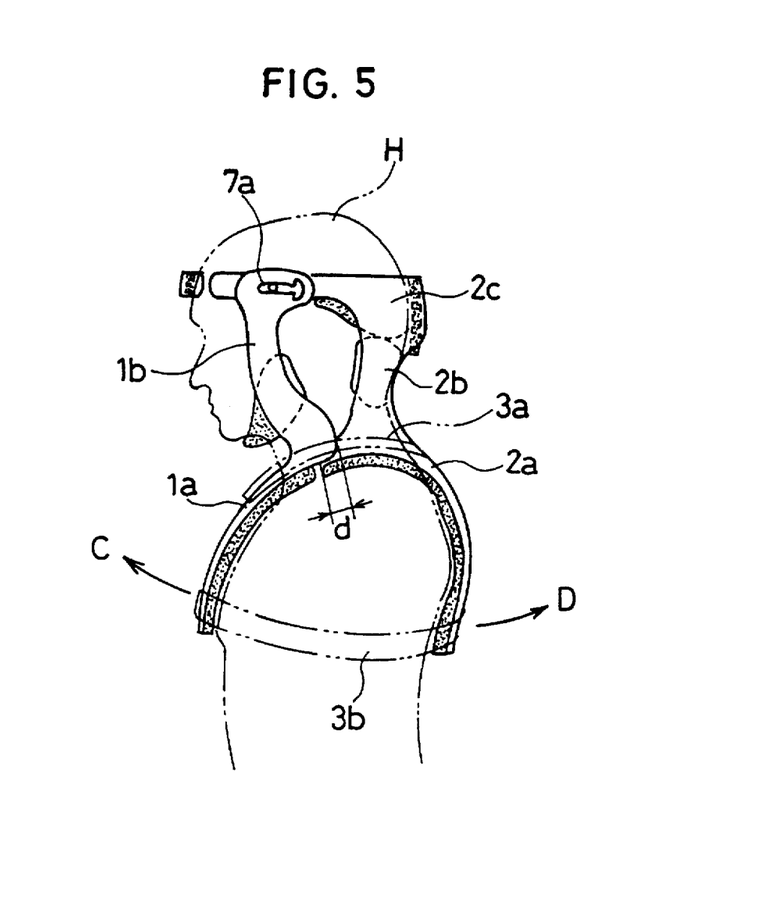
FIG. 5 is a side view of the second embodiment of the cervical orthosis shown in FIG. 2.

As illustrated in FIG. 5, the cervical orthosis of the present invention can be opened in the directions indicated by the arrows C and D while the pin 6 of the rear cervical orthosis member 2 being fit into the slit 7a of the front cervical orthosis member 1. With such a construction, the orthosis in the opened state is put on from the head of the patient H and the slit 7a is located and secured according to the size of the head. Thus, the cervical orthosis can be comfortably fit to the patient H covering the part from the head to the neck.

Band-like belts 3a, 3b are used for securely interconnecting the front and rear cervical orthosis members 1 and 2 while the orthosis being put on the patient. The band-like belt 3a is used to fix the shoulders of the front cervical orthosis member 1 and those of the rear cervical orthosis member 2, while the band-like belt 3b allows the lower end of the front cervical orthosis member 1 to communicate with that of the rear cervical orthosis member 2 so as to fix the brace to the chest. One side of VELCRO fastener is affixed in an insular pattern to the above-mentioned shoulders and the lower ends of the front and rear cervical orthosis members 1 and 2, and the other is affixed to the entire length of the band-like belts 3a, 3b. Such VELCRO fastener is bonded to interconnect the front and rear cervical orthosis members 1 and 2 in a desired position according to the thickness of the chest of the patient.

FIG. 5 shows the state in which the patient puts on the cervical orthosis of this embodiment according to the present invention constructed as described above. In such a state, the back support 2a abuts against the region from the shoulders to the back; the rear supporting portions 2b, 2b abut against both side portions of the posterior of neck, respectively; and the occipital region brace portion 2c of the rear cervical orthosis member 2 abuts against the occipital region. On the other hand, the chest support 1a abuts against the region from the shoulders to the chest, and the front supporting portions 1b, 1b abut against both side portions of the anterior of neck and the side portions of the head. The top end of the chest support 1a and that of the back support 2a have the overlapped portion "d".

Figure 6:
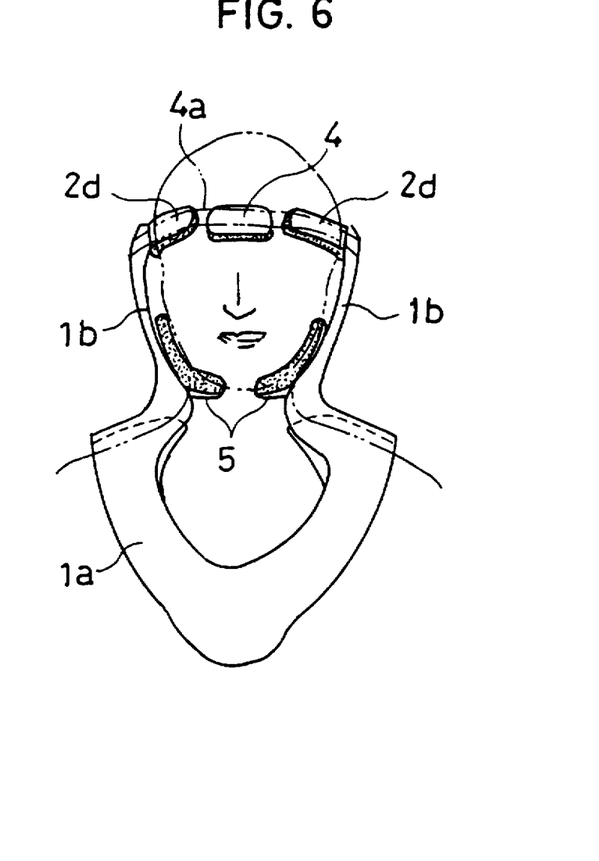
FIG. 6 is a front view of the second embodiment of the cervical orthosis shown in FIG. 2.

As illustrated in FIG. 6, the forehead brace member 4 abuts against the forehead, and the cheek bone brace members 5, 5 abut against the cheek bones so as to support them from an oblique downward angle. The brace members thus abut against the respective regions so that the cervical spine can be reliably and stably braced from the peripheral regions.

Figure 7:
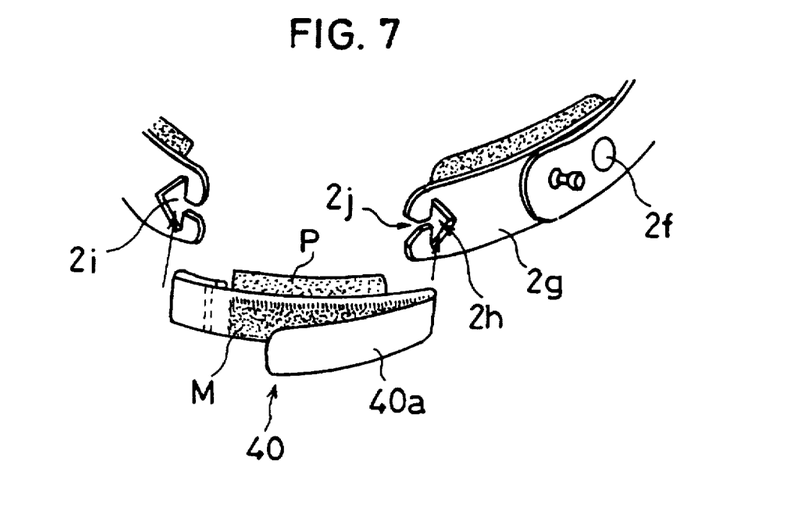
FIG. 7 is a perspective view of a first modification of a forehead brace member according to the second embodiment.

FIG. 7 illustrates a first modification of the forehead brace member 4. The forehead brace member 40 shown in FIG. 7 comprises a band-like belt 40a having VELCRO fastener M affixed to the surface thereof and a pad P affixed to the reverse surface of the band-like belt 40a. A projection 2g has a triangular notch 2h formed at the forward end thereof. With such a construction, one end of the band-like belt 40 passes through a notch 2i and is anchored, and the other end thereof passes through the notch 2h and is folded back so as to be anchored by the VELCRO fastener M, thereby firmly bracing the forehead further. The band-like belt 40a can be fit into the notches 2h and 2i simply by pushing the belt 40a along clearances 2j. The notches 2h and 2i are formed in the same shape so that both right-handed and left-handed patients can equally use the belt 40a.

Figure 8:
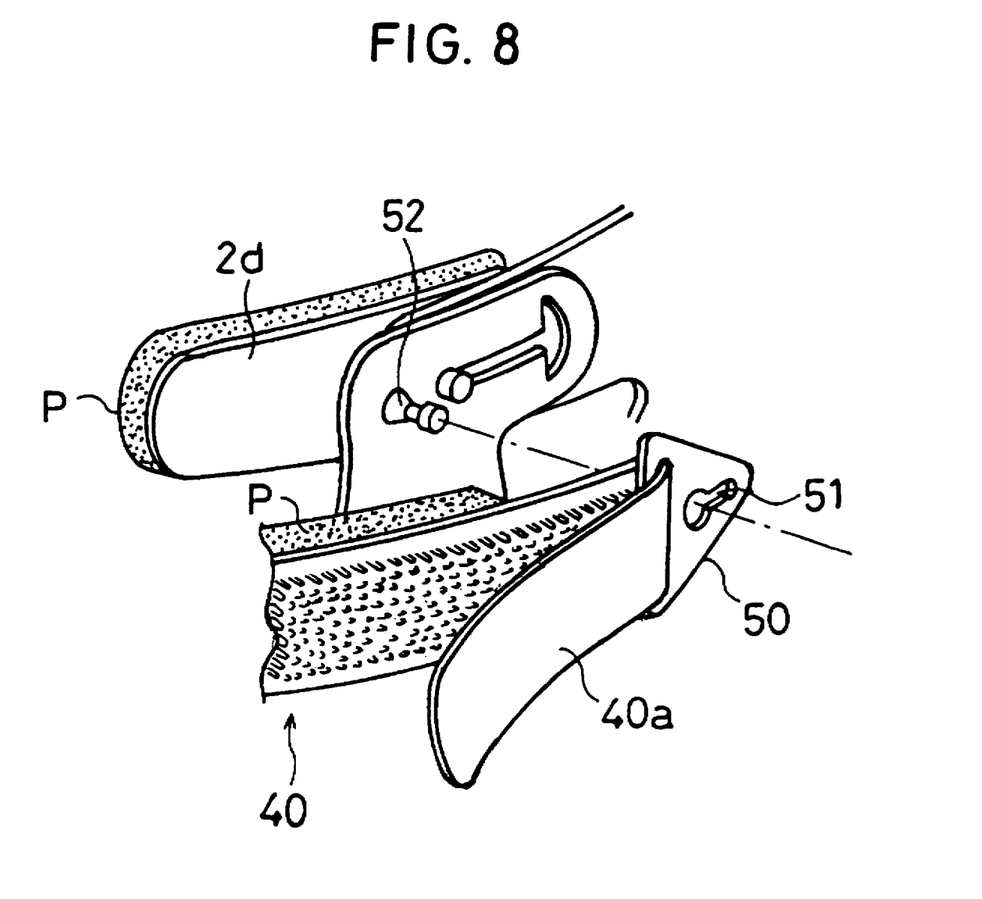
FIG. 8 is a perspective view of a second modification of the forehead brace member.

FIG. 8 illustrates a second modification of the forehead brace member 4. In FIG. 8, the band-like belt 40a is the same as that shown in FIG. 6. In this modification, a pin 52 provided for the front supporting portion 1b is fit into a key-hole shaped notch 51 formed on a triangular element 50, followed by passing one end of the band-like belt 40a into a slit of the triangular element 50, thus adjusting the length of the belt 40a, which is then anchored. The other end of the band-like belt 40a is anchored to another triangular element 50. The exchange of such right and left triangular elements 50 enables both right-handed and left-handed patients to easily anchor the forehead brace member.

Figure 9:
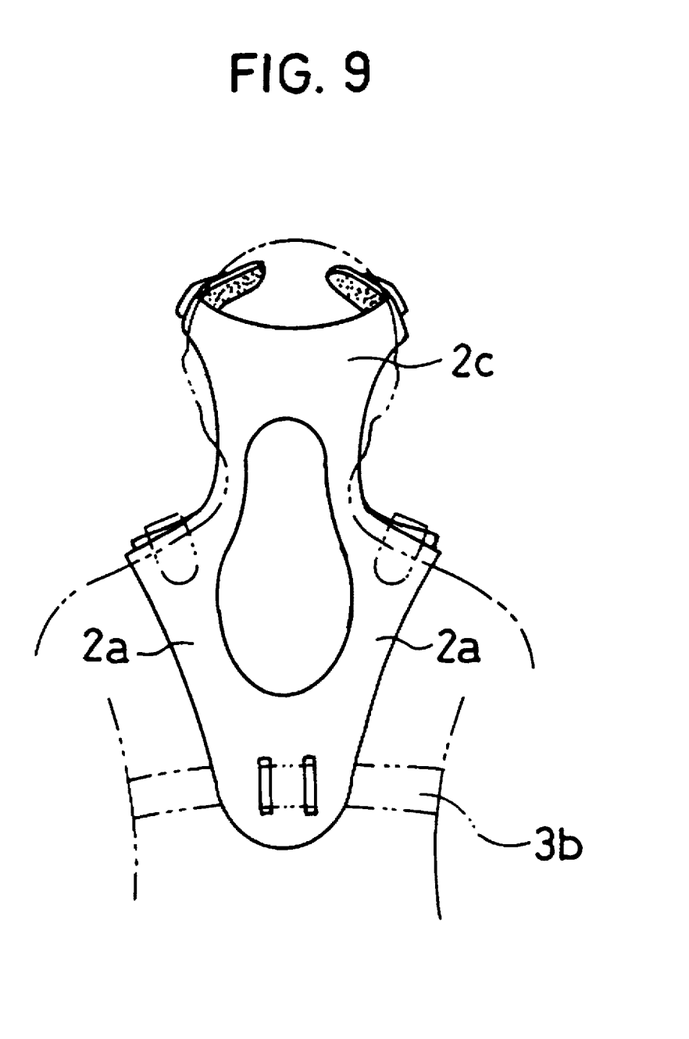
FIG. 9 is a rear view of the second embodiment of the cervical orthosis shown in FIG. 2.

FIG. 9 is a rear view of the foregoing cervical orthosis which is put on the patient.

In the present invention, the following modes may also be added to the above embodiments indicative of the basic constructions. A first mode is provided with an extension element at the bottom of the chest support and/or back support so as to extend the length of the chest support and/or the back support. A second mode is provided with an expansion and contraction element for the front supporting portions 1b and/or the rear supporting portions 2b so as to adjust the length of the supporting portions 1b and/or 2b. A third mode is provided with an interconnecting portion, which length is adjustable, so as to interconnect the parts of the front supporting portions 1b corresponding to the mandible.

Figure 10:
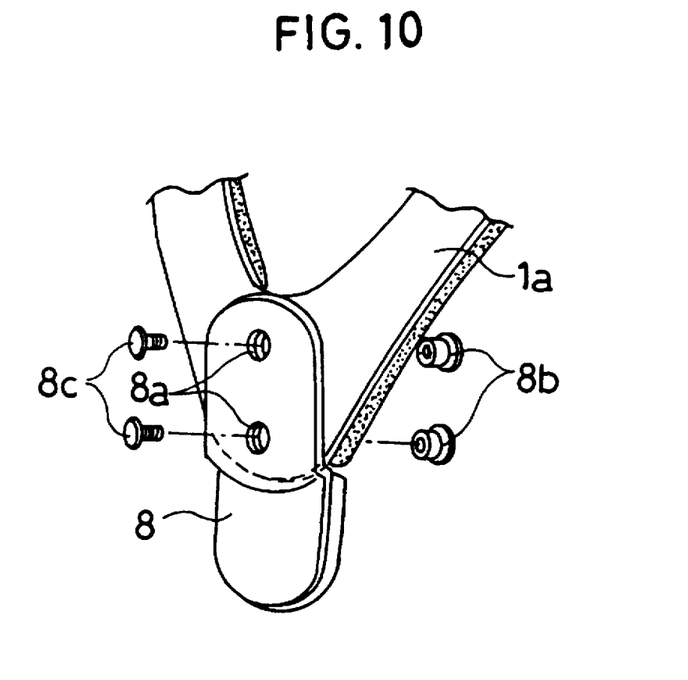
FIG. 10 is a perspective view of the construction of an extension element for a chest support according to the second embodiment.

FIG. 10 shows the first mode. An extension element 8 to be attached to the bottom of the chest support 1a is formed of a tongue-like portion having through-holes 8a, 8a. Mating through-holes are provided for the chest support 1a to be compatible with the through-holes 8a, 8a. The respective through-holes are first positioned. Then plugs 8b, 8b respectively having thread are inserted into such through-holes, and male screws 8c, 8c are screwed into the thread of plugs, thereby extending the length of the chest support 1a and enhancing further secure bracing. Such a construction is also applicable to the extension of the length of the back support 2a.

In the second mode, the present invention may be constructed to have an expansion and contraction element provided for the front supporting portions 1b and/or the rear supporting portions 2b so as to adjust the length of such supporting portions 1b and/or 2b. Any desired expansion and contraction mechanism, except for metal elements, can be used as long as it is constructed to change the length of the supporting portions 1b and/or 2b without impairing the strength of such supporting portions. The length of the front or rear supporting portions is varied so that the resultant brace is able to cope with any length of the neck, and that it is also substantially provided with a tilt mechanism relative to the head.

Figure 11:
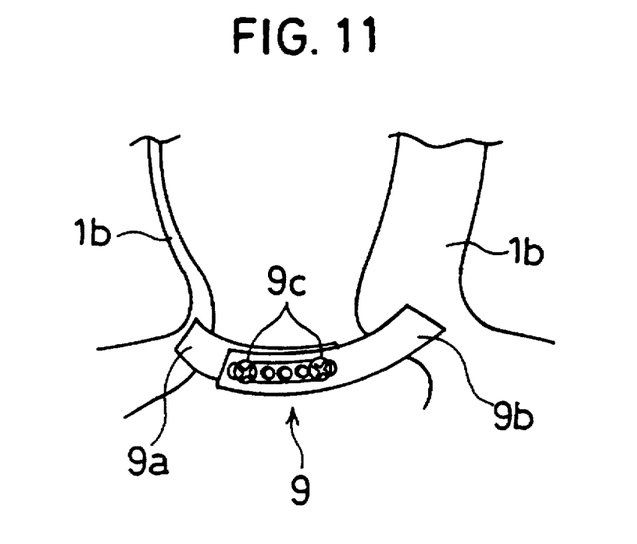
FIG. 11 is a perspective view of a front interconnecting mechanism according to the second embodiment.

FIG. 11 illustrates the third mode. In FIG. 11, an interconnecting element 9 comprises a right band-like portion 9b projecting from one front supporting portion 1b, a left band-like portion 9a projecting from the other front supporting portion 1b, and bolts 9c, 9c for fixing such band-like portions 9a and 9b at a desired overlapped portion. More specifically, a plurality of thread are arranged on the left band-like portion 9a at regular intervals, while a slit having a narrower width than the head of the bolt 9c is formed on the right band-like portion 9b. With such a construction, the overlapped portion of the right and left band-like portions 9a and 9b is adjusted according to the size of the face of the patient and the two bolts 9c, 9c are screwed into the respective two threads, thereby securely bracing the front supporting portions 1b, 1b which is fit to the patient.

Figure 12:
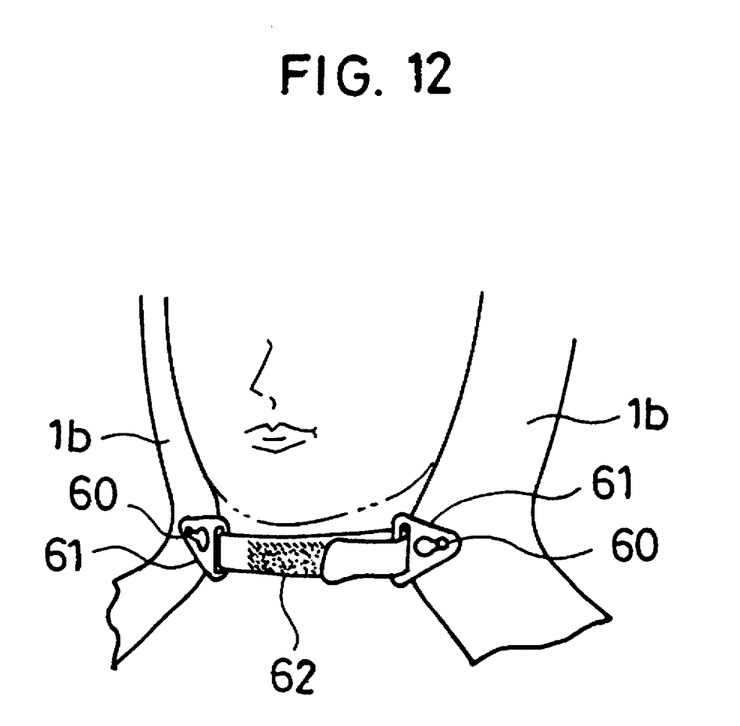
FIG. 12 is a perspective view of another example of the front interconnecting mechanism.

FIG. 12 illustrates a modification of the interconnecting element shown in FIG. 11. In such a modification, pins 60, 60 are provided for the parts of the front supporting portions 1b, 1b corresponding to the mandible. Triangular elements 61, 61 are fit into the respective pins 60, 60, and a band-like belt 62 passes through slits of the triangular elements 61, 61, the length of the band-like belt 62 being adjusted and then anchored by Velcro fastener.

The front and rear cervical orthosis members 1 and 2 require sufficient strength to reliably perform a bracing function required for a cervical orthosis, though a too heavy brace burdens the patient. Therefore, a synthetic resin material is preferably selected to form the orthosis. The thickness of such a synthetic resin material is generally approximately from 2 to 7 mm, and more preferably, approximately from 3 to 5 mm, though it varies depending on the type of resin.

A plurality of punching holes may be provided for the respective front and rear cervical orthosis members 1 and 2, thereby achieving the light weight of the orthosis and also enhancing breathability.

Japanese Applications HEI 6-54113 filed on Mar. 24, 1994 and HEI 6-207452 filed on Aug. 31, 1994 are herein incorporated by reference.

What is claimed is:

1. A cervical orthosis comprising:

(a) a front cervical orthosis member including a chest support abutting against the region from the shoulders to the chest, and two front supporting portions continuously extending from said chest support along both side portions of the anterior of the neck and both side portions of the head;

(b) a rear cervical orthosis member including a back support abutting against the region from the shoulders to the back, two rear supporting portions continuously extending from said back support along both side portions of the posterior of the neck, and an occipital region brace portion provided with the upper end of each of said rear supporting portions, and circumferentially extending against said occipital region so as to brace the occipital region;

(c) an interconnecting member interconnecting the upper end of said front supporting portions with said occipital region brace portion;

(d) a forehead brace member connecting each upper end of said front supporting portions, abutting against the forehead and bracing the frontal region of the head; and (e) a cheek brace member arranged on the internal surfaces of said front supporting portions so as to brace the cheeks without disturbing the movement of the mandible, wherein said cheek brace member is separate and independent from said front supporting portions and anchored to the internal surfaces of said front supporting portions via detachable tape so that it is adjustable to be positioned in a range from the cheeks to the mandible on the internal surface of said front supporting portions.

2. A cervical orthosis according to claim 1, wherein a pair of projections are arranged at front sides of said occipital region brace portion.

3. A cervical orthosis according to claim 1, wherein said forehead brace member includes a belt and a pad detachably attached to said belt.

4. A cervical orthosis according to claim 1, wherein an extension element is arranged at the bottom of said chest support and said back support so as to extend said chest support and said back support.

5. A cervical orthosis according to claim 1, wherein an expansion and contraction element is arranged at said front supporting portions and/or said rear supporting portions so as to adjust the length of said supporting portions.

6. A cervical orthosis according to claim 1, wherein an interconnecting element, which length is adjustable, is arranged to interconnect the parts of said front supporting portions corresponding to the mandible.

7. A cervical orthosis according to claim 1, wherein said interconnecting member includes a pin arranged on the external surface of the front end of said occipital region brace portion, and a mating hole arranged on the upper end of each of said front supporting portions, said pin being inserted into said mating hole, thereby combining said occipital region brace portion and said front supporting portions and allowing a pivotal opening and closing about said pin in the forward-backward direction.

8. A cervical orthosis according to claim 1, wherein a belt is arranged to interconnect said front cervical orthosis member and said rear cervical orthosis member.

9. A cervical orthosis according to claim 1, wherein said interconnecting member includes a pin arranged on the upper end of each of said front supporting portions, and a mating hole arranged on the external surface of the front end of said occipital region brace portion, said pin being inserted into said mating hole, thereby combining said occipital region brace portion and said front supporting portions and allowing a pivotal opening and closing about said pin in the forward-backward direction.

10. A cervical orthosis comprising:

(a) a front cervical orthosis member including a V-shaped chest support extending from the shoulder along the chest, and a pair of front supporting portions continuously extending from the shoulder side of said chest support to both side portions of the head;

(b) a rear cervical orthosis member including a V-shaped back support abutting against the region from the shoulders to the back, a pair of rear supporting portions continuously extending from said back support through sides of the occipital region and an occipital region brace portion extending between the upper end of each of said rear supporting portions so as to circumferentially brace the occipital region:

(c) an interconnecting member for connecting upper ends of said front supporting portions and said rear supporting portions;

(d) a fastening member for allowing the upper end of said front supporting portions and said occipital region of said rear supporting portions to circumferentially brace the head;

(d) cheek brace members opposed to each other disposed on the internal surfaces of said front supporting portions via detachable tape so as to adjust the position of said cheek brace members in a range from the cheek to the mandible for bracing the cheeks from lateral sides thereof without disturbing the movement of the mandible.

11. A cervical orthosis according to claim 10, wherein a pair of projections are vertically pivotable around frontal end portions of said occipital region brace portion, whereby an angle of said projections is adjustable when said projections are interconnected by said fastening member to brace the head.

12. A cervical orthosis according to claim 10, wherein said fastening member has a belt and a cushion detachably attachable to said interior of said belt.

13. A cervical orthosis according to claim 10, wherein said interconnecting member includes a pin arranged on the external surface of a front end of said occipital region brace portion, and a mating hole arranged on the upper end of each of said front supporting portions, said pin being inserted into said mating hole, thereby combining said occipital region brace portion and said front supporting portions and allowing a pivotal opening and closing about said pin in the forward-backward direction.

14. A cervical orthosis according to claim 10, wherein a belt is arranged to interconnect said front cervical orthosis member and said rear cervical orthosis member.

* * * * *

UNITED STATES PATENT AND TRADEMARK OFFICE
CERTIFICATE OF CORRECTION

PATENT NO.   : 5,575,763
DATED        : Nov. 19, 1996
INVENTOR(S)  : Hiroto NAGATA, et al.

It is certified that error appears in the above-indentified patent and that said Letters Patent is hereby corrected as shown below:

On the title page, in Item [75], the third inventor's residence should read:

--Katano--

Signed and Sealed this

Twenty-fifth Day of March, 1997

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,575,763
DATED : November 19, 1996
INVENTOR(S) : Hiroto NAGATA, et al.

It is certified that error appears in the above-indentified patent and that said Letters Patent is hereby corrected as shown below:

On the title page, in Item [75], the fourth inventor's residence should read:

--Toyonaka--

Signed and Sealed this

Twelfth Day of August, 1997

Attest:

BRUCE LEHMAN

*Attesting Officer*   *Commissioner of Patents and Trademarks*